United States Patent
Löscher et al.

(10) Patent No.: US 11,510,855 B2
(45) Date of Patent: Nov. 29, 2022

(54) TOPICAL SUNSCREEN FORMULATION

(71) Applicant: DERMALIQ THERAPEUTICS, INC., Wilmington, DE (US)

(72) Inventors: Frank Löscher, Schriesheim (DE); Ralf Grillenberger, Nuremberg (DE); Chiara Silvana Leo, Heidelberg (DE); Markus Beier, Weinheim (DE)

(73) Assignee: DERMALIQ THERAPEUTICS, INC., Wilmington, DE (US)

( * ) Notice: Subject to any disclaimer, the term of this patent is extended or adjusted under 35 U.S.C. 154(b) by 0 days.

(21) Appl. No.: 17/280,055

(22) PCT Filed: Sep. 20, 2019

(86) PCT No.: PCT/EP2019/075358
§ 371 (c)(1),
(2) Date: Mar. 25, 2021

(87) PCT Pub. No.: WO2020/064556
PCT Pub. Date: Apr. 2, 2020

(65) Prior Publication Data
US 2021/0308024 A1 Oct. 7, 2021

(30) Foreign Application Priority Data
Sep. 27, 2018 (EP) ..................... 18197171

(51) Int. Cl.
| | | |
|---|---|---|
| *A61K 8/31* | (2006.01) | |
| *A61K 8/27* | (2006.01) | |
| *A61K 8/29* | (2006.01) | |
| *A61K 8/34* | (2006.01) | |
| *A61K 8/42* | (2006.01) | |
| *A61K 8/67* | (2006.01) | |
| *A61K 8/92* | (2006.01) | |
| *A61Q 17/04* | (2006.01) | |
| *A61Q 19/00* | (2006.01) | |

(52) U.S. Cl.
CPC ............... *A61K 8/315* (2013.01); *A61K 8/27* (2013.01); *A61K 8/29* (2013.01); *A61K 8/347* (2013.01); *A61K 8/42* (2013.01); *A61K 8/671* (2013.01); *A61K 8/678* (2013.01); *A61K 8/922* (2013.01); *A61Q 17/04* (2013.01); *A61Q 19/004* (2013.01); *A61K 2800/48* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 2,616,927 A | 11/1952 | Kauck et al. | |
| 5,077,036 A | 12/1991 | Long | |
| 5,152,997 A | 10/1992 | Elbert et al. | |
| 5,254,338 A | 10/1993 | Sakai et al. | |
| 5,326,566 A | 7/1994 | Parab | |
| 5,340,567 A | 8/1994 | Cole et al. | |
| 5,518,731 A | 5/1996 | Meadows | |
| 5,667,809 A | 9/1997 | Trevino et al. | |
| 5,874,469 A | 2/1999 | Maniar et al. | |
| 5,874,481 A | 2/1999 | Weers et al. | |
| 5,904,933 A | 5/1999 | Riess et al. | |
| 5,980,936 A | 11/1999 | Krafft et al. | |
| 6,042,845 A | 3/2000 | Sun et al. | |
| 6,060,085 A | 5/2000 | Osborne | |
| 6,113,919 A | 9/2000 | Reiss et al. | |
| 6,159,977 A | 12/2000 | Reeves | |
| 6,224,887 B1 | 5/2001 | Samour et al. | |
| 6,262,126 B1 | 7/2001 | Meinert | |
| 6,391,879 B1 | 5/2002 | Reeves | |
| 6,486,212 B2 | 11/2002 | Meinert | |
| 6,489,367 B1 | 12/2002 | Meinert | |
| 8,029,977 B2 | 10/2011 | Meinert et al. | |
| 8,470,873 B2 | 6/2013 | Chen | |
| 8,759,281 B2 | 6/2014 | Bonnet et al. | |
| 8,986,738 B2 | 3/2015 | Meinert | |
| 9,186,305 B1 | 11/2015 | Suzuki | |
| 9,308,262 B2 | 4/2016 | Günther et al. | |
| 9,757,459 B2 | 9/2017 | Günther et al. | |
| 9,757,460 B2 | 9/2017 | Günther et al. | |
| 9,770,508 B2 | 9/2017 | Günther et al. | |
| 10,130,707 B2 | 11/2018 | Günther et al. | |
| 10,273,298 B2 | 4/2019 | Günther et al. | |
| 10,449,164 B2 | 10/2019 | Günther et al. | |
| 10,507,132 B2 | 12/2019 | Graf et al. | |
| 11,273,174 B2 | 3/2022 | Loscher et al. | |

(Continued)

FOREIGN PATENT DOCUMENTS

| | | |
|---|---|---|
| CN | 106176937 | 12/2016 |
| EP | 0 433 086 | 12/1990 |

(Continued)

OTHER PUBLICATIONS

Sengupta et al., Comprehensive view on chemistry, manufacturing & applications of lanolin extracted from wool pretreatment, 2014, American Journal of Engineering Research, vol. 3, Issue 07, pp. 33-43 (Year: 2014).*
Bardin et al., "Long-Range Nanometer-Scale Organization of Semifluorinated Alkane Monolayers at the Air/Water Interface," Langmuir, 2011, 27, 13497-13505.
Bertilla et al., "Semifluorinated Alkanes as Stabilizing Agents of Fluorocarbon Emulsions," Springer, Tokyl, 2005, International Symposia for Life Sciences and Medicine, vol. 12, pp. 237-251.
Broniatowski, M. et al., "Langmuir Monolayers Characteristic of (Perfluorodecyl)-Alkanes," Journal of Physical Chemistry B, 2004, 108, 13403-13411.
Chuanfu, Y., "Pharmaceutics," People's Medical Publishing House, 1986.

(Continued)

*Primary Examiner* — Nannette Holloman
(74) *Attorney, Agent, or Firm* — Hoxie & Associates LLC

(57) ABSTRACT

The present disclosure relates to topical sunscreen formulations comprising a semifluorinated alkane and a metal oxide selected from titanium dioxide, zinc oxide or mixtures thereof.

29 Claims, No Drawings

(56) References Cited

U.S. PATENT DOCUMENTS

| | | |
|---|---|---|
| 2002/0004063 A1 | 1/2002 | Zhang |
| 2003/0027833 A1 | 2/2003 | Cleary et al. |
| 2003/0170194 A1 | 9/2003 | Piotrowiak |
| 2004/0101551 A1 | 5/2004 | Selzer |
| 2004/0265362 A1 | 12/2004 | Susilo |
| 2005/0075407 A1 | 4/2005 | Tamarkin et al. |
| 2005/0079210 A1 | 4/2005 | Gupta |
| 2005/0084553 A1 | 4/2005 | Moon et al. |
| 2005/0175541 A1 | 8/2005 | Lanza et al. |
| 2006/0078577 A1 | 4/2006 | Dechow |
| 2006/0153905 A1 | 7/2006 | Carrara et al. |
| 2006/0204458 A1* | 9/2006 | Holloway ............... A61K 8/29 424/59 |
| 2008/0019926 A1 | 1/2008 | Krafft et al. |
| 2008/0207537 A1 | 8/2008 | Turner et al. |
| 2008/0254106 A1 | 10/2008 | Bell |
| 2008/0260656 A1 | 10/2008 | Mallard |
| 2009/0104243 A1* | 4/2009 | Utkhede ............... A61L 27/54 424/423 |
| 2009/0169601 A1 | 7/2009 | Koch et al. |
| 2010/0305081 A1 | 12/2010 | Dechow |
| 2011/0269704 A1 | 11/2011 | Seigfried |
| 2012/0100183 A1 | 4/2012 | Schlessinger et al. |
| 2012/0219640 A1 | 8/2012 | Wright |
| 2013/0011484 A1 | 1/2013 | Bevier |
| 2014/0004197 A1 | 1/2014 | Theisinger et al. |
| 2016/0000941 A1 | 1/2016 | Thorsten et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2018/0021434 A1 | 1/2018 | Günther et al. |
| 2019/0125658 A1 | 5/2019 | Ficko |
| 2020/0129543 A1 | 4/2020 | Loscher et al. |
| 2020/0246463 A1 | 8/2020 | Génther et al. |
| 2021/0100904 A1 | 4/2021 | Génther et al. |
| 2022/0079980 A1 | 3/2022 | Loscher et al. |
| 2022/0152096 A1 | 5/2022 | Loscher et al. |

FOREIGN PATENT DOCUMENTS

| | | |
|---|---|---|
| EP | 0 670 159 | 9/1995 |
| EP | 1 152 749 | 4/2006 |
| JP | S5721312 A | 2/1982 |
| JP | H0764702 B2 | 7/1995 |
| JP | 2016-239143 A | 12/2016 |
| RU | 2 111 738 C1 | 5/1998 |
| WO | WO 1998/005301 | 12/1998 |
| WO | WO 2012/007776 | 1/2012 |
| WO | WO 2015/082369 | 6/2015 |
| WO | WO 2017/210777 | 12/2017 |

OTHER PUBLICATIONS

Chemical Book, 5-Fluorouracil, available at <http://www.chemicalbook.com/ChemicalProductProperty_EN_CB8162744,htm>, accessed Mar. 7, 2014, 1 page.

CN106176937A, Liu Yipeng, "Eczema-acne ointment," Dec. 7, 2016, English language machine translation of abstract, Espacenet, date obtained: Apr. 30, 2021, 1 page <https://worldwide.espacenet.com/patent/search/family/058089634/publication/CN106176937A?q=CN106176937A>.

Costa Gomes et al., "Solubility of dioxygen in seven fluorinated liquids," Journal of Fluorine Chemistry, 2004, 125, 1325-1329.

Dembinski, R. et al., "Semi-fluorinated Alkanes as Carriers for Drug Targeting in Acute Respiratory Failure," Experimental Lung Research, 2010, 36, 499-507.

Dias et al., "Solubility of oxygen in liquid perfluorocarbons," Fluid Phase Equilibria, 2004, 222-223;325-330.

Dutescu et al., "Semifluorinated alkanes as a liquid drug carrier system for topical ocular drug delivery," European Journal of Pharmacuetics and Biopharmaceutics, 2014, 88(1):123-128, Abstract Only (2 pages).

Elkeeb, R. et al., "Transungual Drug Delivery: Current Status," International Journal of Pharmaceutics, 2010, 384, 1-8.

English-language machine translation of EP0670159 (A1) issued in U.S. Appl. No. 14/122,025, filed Apr. 1, 2015, 10 pages.

Freiburger Dokumentenserver (FreiDok), Albert-Ludwigs-Unversität Freiburg, retrieved from http://www.freidok.uni-freiburg.de/volltexte/5682/, retrieved on Feb. 5, 2014, 2 pages.

Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.

Gerdenitsch, "Emulsions—established and promising drug carriers for parenteral administration," retrieved from Internet, date accessed: Jun. 20, 2016, URL: <http://ipimediaworld.com/wp-content/uploads/2012/05/Pages-from-IPI-Volume-2-Issue-1-11.pdf>.

Griffin, W., "Classification of Surface-Active Agents by 'HLB'," Journal of the Society of Cosmetic Chemists, 1949, 1, 311-326.

Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf (retrieved on Oct. 10, 2011).

Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).

Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.

Holm, R. et al., "A novel excipient, 1-perfluorohexyloctane shows limited utility for the oral delivery of poorly water-soluble drugs," European Journal of Pharmaceutical Sciences, 2011, 42: 416-422.

International Search Report and Written Opinion for International Application No. PCT/EP2019/075358 dated Sep. 20, 2019, 11 pages.

JPH0764702B2, Kanebo Ltd, "Cosmetic of Polyphasic Emulsion Type," Jul. 12, 1995, English language machine translation of abstract, Espacenet, date obtained: Apr. 30, 2021, 1 page <https://worldwide.espacenet.com/patent/search/family/014142733/publication/JPH0764702B2?q=JPH0764702B2>.

JPS5721312A, Green Cross Corp, "Breathable Ointment," Apr. 2, 1982, English language machine translation of abstract, Espacenet, date obtained: Apr. 30, 2021, 1 page <https://worldwide.espacenet.com/patent/search/family/014132731/publication/JPS5721312A?q=JPS5721312A>.

Knepp, V. et al., "Stability of Nonaqueous Suspension Formulations of Plasma Derived Factor IX and Recombinant Human Alpha Interferon at Elevated Temperatures," Pharmaceutical Research, 1998, 15 (7), 1090-1095.

Kociok, N., et al, "Influence on Membrane-Mediated Cell Activation by Vesicles of Silicone Oil or Perfluorohexyloctane," Graefe's Archive for Clinical and Experimental Ophthalmology, 2005, 243, 345-358.

Mantle et al., "Adverse and beneficial effects of plant extracts on skin and skin disorders," Adverse Drug Reaction and Toxicological Reviews, 2001, 20(2): 89-103.

Meinert, H. et al., "The Use of Semifluorinated Alkanes in Blood-Substitutes," Biomaterials, Artificial Cells, and Immobilization Biotechnology, 1993, 21 (5), 583-595.

Meinert, H. et al., "Semifluorinated Alkanes—A New Class of Compounds with Outstanding Properties for Use in Ophthalmology," European Journal of Ophthalmology, 2000, 10 (3), 189-197.

Messmer, et al. "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).

Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.

(56) References Cited

OTHER PUBLICATIONS

Murdan, S., "Enhancing the Nail Permeability of Topically Applied Drugs," Expert Opinion on Drug Delivery, 2008, 5 (11), 1267-1282.
Plassmann, M. et al., "Trace Analytical Methods for Semifluorinated n-Alkanes in Snow, Soil, and Air," Analytical Chemistry, 2010, 82(11), 4551-4557.
Plassmann, M. et al., "Theoretical and Experimental Simulation of the Fate of Semifluorinated n-Alkanes During Snowmelt," Environmental Science & Technology, 2010, 44 (17), 6692-6697.
Rosca-Casian, O. et al., "Antifungal Activity of *Aloe vera* Leaves," Fitoterapia, 2007, 28, 219-222.
RU2111738C1, Aktsionerone Obshchestvo Nizar, "Product to Enhance Sun-Protecting Activity of Photo-Protecting Agents," May 27, 1998, English language machine translation of abstract, Espacenet, date obtained: Apr. 30, 2021, 1 page <https://worldwide.espacenet.com/patent/search/family/020182059/publication/RU211173 8C1?q=RU2111738C1>.
Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, 2003, 19:4889-4894.
Steven, P. et al. "Semifluorinated Alkane Eye Drops for Treatment of Dry Eye Disease—A Prospective, Multicenter Nonintervention Study" Journal of Ocular Pharmacology and Therapeutics (2015) vol. 31(8):498-503.
Steven et al., "Semifluorinated Alkane Eye Drops for Treatment of Dry Eye Disease Due to Meibomian Gland Disease," Journal of Ocular Pharmacology and Therapeutics, 2017, 33(9):1-8.
Stevenson, C., "Characterization of Protein and Peptide Stability and Solubility in Non-Aqueous Solvents," Current Pharmaceutical Biotechnology, 2000, 1, 165-182.
Thomas et al., "The therapeutic uses of topical vitamin A acid," Journal of the American Academy of Dermatology, 1981, 4(5): 505-513.
Ujiie et al., "Successful Treatment of Nail Lichen Planus with Topical Tacrolimus", Department of Dermatology, Hokkaido University Graduate School of Medicine, 2009.
Wong, D. et al., "Perfluorocarbons and Semifluorinated Alkanes," Seminars in Ophthalmology, 2000, 15 (1), 25-35.
Xiangqun, J. et al., "Professional Knowledge on Pharmaceutical Field," Military Medical Science Press, 2009, vol. 2.
Yaoxue Zhuanye Zhishi II (Editor: Jin Xiangqun), Military Medical Science Press, $1^{st}$ Printing of $2^{nd}$ Edition, Mar. 2009, p. 158.
Yaoxue Zhuanye Zhishi II (Editor: Jin Xiangqun), Military Medical Science Press, $1^{st}$ Printing of $2^{nd}$ Edition, Mar. 2009, p. 158, 3 pages (English Machine Translation).
Zakeri et al., "Topical calcipotriol therapy in nail psoriasis", A study of 24 cases, Dermatology Online Journal, 11(3):5; 2005.
Zhang et al., "Surface micelles of semifluorinated alkanes in Langmuir-Blodgett monolayers," Phys. Chem. Chem. Phys., 2004, 6, 1566-1569.

* cited by examiner

TOPICAL SUNSCREEN FORMULATION

CROSS-REFERENCE TO RELATED APPLICATIONS

This application is a U.S. National Stage application under 35 U.S.C. § 371 of International Application No. PCT/EP2019/075358, filed on Sep. 20, 2019, which claims priority to and the benefit of European Application No. 18197171.4, filed on Sep. 27, 2018, the contents of which are hereby incorporated by reference in its entireties.

The present disclosure is in the field of topical sunscreen formulations.

BACKGROUND OF THE INVENTION

Human skin is sensitive to sunlight and artificial light in the wavelengths range between about 290 and 400 nm (uv light). Prolonged exposure to uv lights causes serious skin conditions from erythema, sunburns, reddening, blisterings to carcinomas. Since increased incidence in skin cancer cases, such as squamous and basal cell carcinomas, has been reported worldwide, use of photoprotective agents has increased over the years. Photoprotective agents are commonly used either therapeutically or prophylactically.

A sunscreen, also known as sunblock, is a topical product that absorbs or reflects some of the sun's ultraviolet (UV) radiation and thus helps protect against sunburns. A sunscreen typically comprises UV blockers or absorbers to reduce the negative impacts on the skin from the sun such as burning, wrinkles and cancer. Ideal sun screening agents should be safe, chemically inert, non irritating, nontoxic, photostable, invisible, non-staining, non-greasy, and able to provide complete protection to the skin against damage from solar radiation. They should be formulated in a cosmetically acceptable form and ingredients should remain on the upper layers of the skin even after sweating and swimming. They should also effectively block both UVB and UVA rays.

Generally, sunscreens are available in the form of creams, lotion, gels, ointments, pastes, oils, butters, sticks, and sprays. Spray or gel-based sunscreens are preferred in oily skin and acne.

Common actives which are included in sunscreens are titanium dioxide, zinc oxide, avobenzone, benzophenone 8, octocrylene and oxybenzone, together with other agents like moisturising agents, humectants and emollients. Inorganic chemicals like titanium dioxide and zinc oxide absorb and scatter uv rays, unlike organic chemicals which only absorb. When a sunscreen lotion is put on the skin, it forms a continuous film which provides protection from UV rays. Ideally, this film will spread easily and will be resistant to wash-off.

When formulating a sunscreen, various factors should be considered like the solubility and stability of some uv filters and, being cosmetic items, also the sensorial aspects. The ideal aim is the highest possible protection with the minimum possible amount of uv filters. Moreover, a high amount of sunscreen ingredients is often associated to a bad, like greasy or waxy, final perception of the skin. (Cosmetics 2017, 4, 15). Ease of application and cosmetic appeal are important in formulating sunscreen compositions. A sunscreen formulation should rub in easily, be non-sticky and invisible on the skin after application.

EP0433086 B1 describes sunscreen compositions comprising mixtures of titanium dioxide and zinc oxide. EP 3145473 B1 relates to sunscreen products comprising multilayer type encapsulations containing pigments in which excessive whiteness due to titanium dioxide and zinc oxide is visually masked upon skin application.

SUMMARY OF THE INVENTION

The objective of the present invention is to provide improved sunscreen formulations, which at the same time address and overcome the various issues and at least one of the limitations or disadvantages associated with prior art sunscreen formulations. In particular, the objective of the present invention is to provide a sunscreen formulation which is invisible after application on the skin, non-staining and non-greasy and which may be used to prevent skin disorders deriving from the exposure to the uv light. The objective of the present invention is attained by the claims.

Without wishing to be bound by theory, the advantages of the sunscreen formulation of the present invention include a) quick penetration into the skin (stratum corneum), (b) complete penetration into the stratum corneum, leaving no whitish residues of the metal oxides on the surface of the skin, (c) therefore no discoloration or grease spots on textiles/clothing, (d) leaving a silky feeling on the skin, (e) forming a water-repelling layer, (f) no clogging of the sebaceous glands.

In a first aspect, the present disclosure provides a sunscreen formulation comprising a semifluorinated alkane, a metal oxide selected from titanium dioxide, zinc oxide and any combination thereof, and optionally a co-solvent and/or an oil component and/or an active ingredient.

In a second aspect, the present disclosure provides the use of a sunscreen formulation according to the first aspect of the invention for protecting the skin from sunburn.

In a third aspect the invention provides a sunscreen formulation according to the first aspect of the invention for use as a medicine.

In a fourth aspect, the invention provides a method of protecting and/or preventing the skin from consequences and/or damage caused by UV-radiation, comprising topically administering the sunscreen formulation according to the first aspect of the invention to the skin of a subject.

In a fifth aspect the present disclosure provides a kit comprising the sunscreen formulation according to the first aspect of the invention and a container for holding said sunscreen formulation.

DETAILED DESCRIPTION OF THE INVENTION

In a first aspect the present invention provides a sunscreen formulation comprising a semifluorinated alkane and a metal oxide selected from titanium dioxide, zinc oxide and mixtures thereof.

The term "semifluorinated alkane", also referred to as "SFA" throughout this document, as used herein refers to a linear or branched compound composed of at least one perfluorinated segment (F-segment) and at least one non-fluorinated hydrocarbon segment (H-segment). Preferably, the semifluorinated alkane is a linear or branched compound composed of one perfluorinated segment (F-segment) and one non-fluorinated hydrocarbon segment (H-segment). Preferably, said semifluorinated alkane is a compound that exists in a liquid state within the temperature range of 4° to 40° C. In one embodiment, the perfluorinated segment and/or the hydrocarbon segment of the said SFA optionally comprises or consists of a cyclic hydrocarbon segment, or optionally said SFA comprises an unsaturated moiety within the hydrocarbon segment.

It is preferred that the F- and the H-segment of the linear or branched semifluorinated alkane comprise, independently from one another, 2 to 10 carbon atoms.

According to a preferred embodiment of the present invention, the semifluorinated alkane is a linear compound of the formula (I) CF3(CF2)n(CH2)mCH3, wherein n and m are integers independently selected from each other from the range of 2 to 10.

According to another nomenclature, the linear semifluorinated alkane may be referred to as FnHm, wherein F means the perfluorinated hydrocarbon segment, H means the non-fluorinated hydrocarbon segment and n, m is the number of carbon atoms of the respective segment. For example, F4H5 is used for 1-perfluorobutyl-pentane. In a preferred embodiment of the present invention, the semifluorinated alkane is a semifluorinated alkane of formula (I) CF3(CF2)n(CH2)mCH3 wherein n is selected from 3 to 5 and m is selected from 4 to 9. More preferred is a semifluorinated alkane selected from F4H5, F4H6, F4H8, F4H10, F6H8, F6H10 and combinations thereof. Most preferred is a semifluorinated alkane selected from F4H8, F6H8 and F6H10. Even most preferred is F6H8, 1-perfluorohexyloctane.

Preferably the formulation of the present invention comprises a semifluorinated alkane at a concentration of from 45 to 95 percent by weight, more preferably from 50 to 95 percent by weight, even more preferably from 70 to 95 percent by weight based on the total weight of the formulation. Most preferably, the semifluorinated alkane is present at a concentration of from 80 to 95 percent by weight based on the total weight of the formulation.

In a preferred embodiment, the semifluorinated alkane is present at a concentration of at least 45 percent by weight, preferably at least 50 percent by weight, more preferably at least 70 percent by weight, most preferably at least 80 percent by weight based on the total weight of the formulation.

The sunscreen formulation of the present invention comprises a metal oxide selected from titanium dioxide, zinc oxide and mixtures thereof. The metal oxide may be present at a concentration of from 1 to 20 percent by weight with respect to the total weight of the formulation. In a preferred embodiment, the sunscreen formulation of the present invention comprises titanium dioxide or zinc oxide or mixtures thereof at a concentration of from 1 to 20 percent by weight, preferably of from 1 to 10 percent by weight based on the total weight of the formulation.

In a preferred embodiment, the metal oxide is $TiO_2$. In a more preferred embodiment, the metal oxide is $TiO_2$ at a concentration of from 1 to 10 percent by weight, based on the total weight of the formulation.

In another preferred embodiment, the metal oxide is ZnO. Preferably, ZnO is present at a concentration of from 1 to 20 percent by weight based on the total weight of the formulation.

Preferably the metal oxide has a mean particle diameter in the range of 1 to 100 nm, more preferably in the range of from 1 to 50 nm. In a preferred embodiment, the metal oxide is titanium dioxide having a mean particle diameter of from 1 to 50 nm. In a more preferred embodiment, the metal oxide is titanium dioxide having a mean particle diameter of from 1 to 50 nm at a concentration of from 1 to 10 percent by weight based on the total weight of the formulation.

In the present invention a solid thickening agent may be comprised in the sunscreen formulation. Solid thickeners which may be employed in the present invention comprise plant waxes, animal waxes, petroleum derived waxes, triglycerides, $C_{12-24}$ fatty acids, fatty alcohols, fatty alcohols derivatives and combinations thereof. Non limiting examples of waxes are bees wax, lanolin wax (wool wax), lanolin wax derivatives, carnauba wax, candelilla wax, castor wax, rice bran wax, spermaceti wax, bran wax, montan wax, kapok wax, bay berry wax, shellac wax, sugar cane wax, paraffin wax, ceresin wax.

In a preferred embodiment, the solid thickening agent is selected from plant waxes, animal waxes, petroleum derived waxes, triglycerides, cetyl alcohol, tetradecanol and combinations thereof. More preferably, the solid thickening agent is selected from beeswax, paraffin wax, cetyl alcohol and combinations thereof.

The solid thickening agent may be comprised at a concentration of from 1 to 20 percent by weight, preferably of from 1 to 10 percent by weight based on the total weight of the formulation.

Preferably, the formulation of the present invention does not comprise any preservative.

Water can also be present in the formulation of the present invention, however preferably in small or trace amounts of up to 1.0 percent by weight or even up to 0.1 percent by weight based on the total weight of the formulation. In a preferred embodiment, the formulation of the present invention is essentially free of water, whereas the residual water may be attributed to the potential water content of the chosen active ingredient. The term 'essentially' as used herein means if present then in trace or residual amounts such as to confer no technical advantage or relevance in respect of the object of the invention. In a preferred embodiment the sunscreen formulation is water free.

In a more preferred embodiment, the sunscreen formulation is preservative and water free. Preferably, the sunscreen formulation of the present invention is an ointment, more preferably a water free ointment.

Optionally, the sunscreen formulation of the present invention comprises a cosolvent and/or an oil component and/or an active ingredient.

The formulation of the present invention may further comprise an active ingredient. Preferably, the active ingredient is one selected from panthenol, thymol, tea tree oil, retinol palmitate, tocopherol. More preferably the active ingredient is selected from D-panthenol, retinol palmitate, tocopherol and esters thereof.

The active ingredient may be comprised at a concentration of up to 10 percent by weight, preferably of up to 5 percent by weight, with respect to the total weight of the formulation. In a preferred embodiment, the active ingredient is present at a concentration of from 0.05 to 10 percent by weight, preferably of from 0.05 to 5 percent by weight with respect to the total weight of the formulation.

The sunscreen formulation of the present invention may comprise a cosolvent. In a preferred embodiment, the cosolvent is present at a concentration of up to 10 percent by weight, more preferably up to 5 percent by weight based on the total weight of the formulation. More preferably the cosolvent is present at a concentration of from 0.5 to 10 percent by weight, most preferably of from 0.5 to 5 percent by weight based on the total weight of the formulation.

Examples of cosolvents which may be included in the formulation of the present invention are isopropanol, ethanol, liquid medium chain triglycerides, N-methyl-2-pyrrolidone, diethylene glycol monomethylether, diethylene glycol monoethylether, ethyl acetate, ethyl oleate, octyldodecanol, diethyl sebacate. Preferably, the cosolvent is selected from isopropanol, ethanol, liquid medium chain triglycerides, diethylene glycol monoethylether, diethyl sebacate.

The sunscreen formulation of the present invention may comprise an oily material. Examples of oily materials are squalane, squalene, essential oils, liquid triglycerides, silicone oils like cyclomethicone and dimethicone, mineral oils, emollient vegetable oils such as olive, coconut, jojoba, sesame, avocado, sunflower, safflower, borage, corn, and sea buckthorn oil. In a preferred embodiment, the sunscreen formulation of the present invention comprises an oily material selected from squalane, squalene, silicone oils, mineral oils, essential oils, liquid triglycerides, vegetable oils.

An oily material may be present at a concentration of from 1 to 45 percent by weight, preferably of from 1 to 20 percent by weight, more preferably of from 1 to 10 percent by weight based on the total weight of the formulation.

In a preferred embodiment, the sunscreen formulation of the present invention comprises squalane. Preferably squalane is present at a concentration of from 1 to 45 percent by weight, more preferably from 1 to 20 percent by weight, most preferably from 1 to 10 percent by weight based on the total weight of the formulation.

Emollients like isopropyl myristate and isopropyl palmitate can be included in the formulation of the present invention.

All the embodiments and preferred embodiments relating to the formulation of the first aspect of the invention as described above apply also to any of the following aspects of the present invention.

In a second aspect the present invention provides for the use of the sunscreen formulation according to the first aspect of the invention for protecting the skin from sunburns.

In a third aspect, the present invention provides for the use of the sunscreen formulation according to the first aspect of the invention for use as a medicine. In particular, the formulation according to the first aspect of the present invention may be used in a method of preventing skin cancer, such as melanoma, basal cell carcinoma and squamous cells carcinoma.

In a fourth aspect the disclosure provides a method of protecting and/or preventing the skin from consequences and/or damage caused by UV-radiation, comprising topically administering the sunscreen formulation according to the first aspect of the invention to the skin of a subject.

In a fifth aspect, the present disclosure provides a kit comprising the sunscreen formulation according to the first aspect of the invention and a container for holding the formulation. The container can be for example a jar, a tube, a bottle, a dispenser or other types of containers suitable for holding the formulation. The containers can have for example a pump and/or a squeeze mechanism.

The kit may include a package comprising the container in which the formulation of the first aspect of the present invention is placed. In the package, instructions for use can be included.

In a sixth aspect the present invention provides the formulation according to the first aspect of the invention for use in a method of preventing sunburns and skin cell damage caused by uv radiations. Examples of skin cell damages are photoaging, actinic or solar keratoses. Sunburn, also called erythema, is one of the signs of UV exposure and skin damage. Sunburn is a form of short-term skin damage, characterised by redness and peeling after a few days.

In summary the present invention comprises the following preferred items:

1. A sunscreen formulation, comprising:
    a semifluorinated alkane,
    1-6 wt % of a metal oxide selected from titanium dioxide, zinc oxide and mixtures thereof,
    a solid thickening agent and
    optionally a co-solvent and/or oil component and/or active ingredient.
2. The sunscreen formulation of any preceding items, wherein the semifluorinated alkane is of formula F(CF2)n(CH2)mH, wherein n is an integer from 4-6 and m is an integer from 5-10.
3. The sunscreen formulation of any preceding items, wherein the semifluorinated alkane is selected from 1-perfluorohexyl-octane (F6H8), 1-perfluorbutyl-pentane (F4H5), 1-perfluorohexyl-decane (F6H10), 1-perfluorobutyl-octane (F4H8), 1-perfluorobutyl-decane (F4H10) and combinations thereof.
4. The sunscreen formulation of any preceding items, wherein the semifluorinated alkane is 1-perfluorohexyl-octane (F6H8).
5. The sunscreen formulation of any preceding items, wherein the formulation comprises 50-95 wt % of semifluorinated alkane.
6. The sunscreen formulation of any preceding items, wherein the formulation comprises 80-84 wt % of a semifluorinated alkane, about 4-6 wt % of the metal oxide, 3-8 wt % of the solid thickening agent, preferably 80-84 wt % of 1-perfluorohexyloctane, 4-6 wt % of the metal oxide and 3-8 wt % of the solid thickening agent, based on the total weight of the formulation.
7. The sunscreen formulation of any preceding items, wherein the formulation comprises 80-84 wt % of a semifluorinated alkane, about 4-6 wt % of titanium dioxide, 3-8 wt % of the solid thickening agent.
8. The sunscreen formulation of any preceding items, wherein the metal oxide particles have a mean particle diameter of between 1-100 nm.
9. The sunscreen formulation of any preceding items, wherein the solid thickening agent is a natural or synthetic thickening agent.
10. The sunscreen formulation of any preceding items, wherein the formulation comprises at least 1 wt %, preferably at least 3 wt %, more preferably at least 5 wt % of the solid thickening agent based on the total weight of the formulation.
11. The sunscreen formulation of any preceding items, wherein the formulation comprises at most 40 wt %, preferably at most 30 wt %, more preferably at most 20 wt %, most preferably at most 10 wt % of the solid thickening agent based on the total weight of the formulation.
12. The sunscreen formulation of any preceding items, wherein the natural or synthetic thickening agent is selected from plant waxes, animal waxes, petroleum derived waxes, triglycerides, cetyl alcohol, tetradecanol or combinations thereof.
13. The sunscreen formulation of any preceding items, wherein the thickening agent is a wax selected from the group consisting of bees wax, lanolin (wool wax), carnauba wax, candelilla wax, castor wax, rice bran wax (rice wax), spermaceti wax, jojoba oil, bran wax, montan wax, kapok wax, bay berry wax, shellac wax, sugar cane wax, paraffin wax, ceresin wax.
14. The sunscreen formulation of any preceding items, wherein the total amount of the co-solvent, oil component and the active ingredient in the formulation is up to about 45 wt %, preferably up to about 20 wt %, more preferably up to about 10 wt %.
15. The sunscreen formulation of any preceding items, in form of an ointment.
16. The sunscreen formulation of any preceding items, wherein the sunscreen formulation has a sun protection factor of at least 6.
17. The sunscreen formulation of any preceding items, wherein the formulation is water-free.
18. The sunscreen formulation of any preceding items, wherein the formulation is preservative-free.
19. The sunscreen formulation of any of the preceding items, comprising an active ingredient selected from panthenol, thymol, tea tree oil, retinol palmitate, tocopherol.
20. Use of a sunscreen formulation according to any of the items 1 to 19 for protecting the skin from sunburn.
21. The composition according to any of the items 1 to 19, for use as a medicine.
22. The composition according to any of the items 1 to 19, for use in the prevention of skin cell damage caused by UV-radiation.
23. The composition according to any of the items 1 to 19, for use in the prevention of skin cancer.
24. A method of protecting and/or preventing the skin from consequences and/or damage caused by UV-radiation, comprising topically administering the sunscreen formulation as defined in items 1 to 19 to the skin of a subject.
25. The method of item 24, wherein the method is effective in protecting the skin from sunburn.
26. A method of item 24, wherein the method is effective in preventing skin cell damage caused by UV-radiation.
27. The method of items 24 to 26, wherein the method is effective in preventing the development of skin cancer.
28. A kit comprising the sunscreen formulation as defined in any of the items 1 to 19, and a container for holding the sunscreen formulation.
29. A process for the production of a sunscreen formulation according to any of the preceding items.
30. The process of item 29, comprising the step of
a) mixing all the ingredients
b) heating up till about 80° C.
c) cooling down at room temperature

EXAMPLES

Example 1: Sunscreen Formulations

The ingredients of each formulation were weighed in a suitable container.

The ingredients used in the following formulations are: Paraffin wax (Sigma Aldrich, CAS 8002-74-2), Squalane (Sigma Aldrich, CAS 111-01-3), F6H8 (Novaliq), Cetyl alcohol (Sigma Aldrich, CAS 36653-82-4, 99%), TiO2 (Sigma Aldrich; primary particle size 21 nm; CAS 13463-67-7), beeswax (Acros Organics; CAS 8012-89-3), ZnO (Aliacura; 100-200 nm; CAS 1314-13-2).

TABLE 1

| SC-1 | *wt % |
| --- | --- |
| Beeswax | 2, 2 |
| Paraffin wax | 2, 2 |
| Cetyl alcohol | 2, 2 |
| Squalane | 6, 7 |
| TiO2 | 5, 2 |
| F6H8 | 81, 5 |

*wt % indicates the amount of each ingredient in percent by weight based on the total weight of the composition.

After all ingredients listed in Table 1 are weighed, the container is closed and heated to approx. 80° C. using a waterbath. After visual confirmation that all ingredients, except titanium dioxide, are melted and form a homogeneous mixture, the mixture is taken out of the water bath and allowed to cool down to room temperature. After cooling down, a white semisolid mixture is obtained. Gentle stirring of this mixture leads to an easy applicable formulation.

Following the instructions above, the following sunscreen formulations (SC2-SC5) were prepared:

| SC-2 | wt % |
| --- | --- |
| Beeswax | 2 |
| Paraffin wax | 1, 5 |
| Cetyl alcohol | 1, 5 |
| Squalane | 7 |
| TiO2 | 5 |
| F6H8 | 83 |

| SC-3 | wt % |
| --- | --- |
| Beeswax | 3 |
| ZnO | 5 |
| F6H8 | 92 |

| SC-4 | wt % |
| --- | --- |
| Beeswax | 3, 5 |
| TiO2 | 5 |
| F6H8 | 91, 5 |

| SC-5 | wt % |
| --- | --- |
| Beeswax | 2, 5 |
| Paraffin wax | 2, 5 |
| Squalane | 45 |
| TiO2 | 5 |
| F6H8 | 45 |

Example 2: Administration

The formulations of Example 1 (SC-1 to SC-5) present as highly pleasant semi-solid formulations. When administered to the skin of the forearm, a silky feeling was recognized, with the formulations absorbing very quickly into the skin. While shortly after administration still a white color was observable, within 30-60 seconds this colour completely disappeared after gentle massaging, demonstrating that the formulations including the metal oxides readily penetrated into the stratum corneum, leaving not even traces of the coloring metal oxides on the surface of the skin. Further, after being completely absorbed into the skin, the sunscreen formulations did not leave any unpleasant greasy feeling behind. Contact of the sunscreen skin with textiles/clothing did not lead to discoloration or greasy spots.

The invention claimed is:

1. A sunscreen formulation, comprising
   a) a semifluorinated alkane;
   b) a metal oxide selected from titanium dioxide, zinc oxide and mixtures thereof; and
   c) optionally a co-solvent and/or an oil component and/or an active ingredient;
   wherein the semifluorinated alkane is a compound of formula CF3(CF2)n(CH2)mCH3, wherein n and m are integers independently selected from each other from the range of 2 to 10.

2. The sunscreen formulation of claim 1, wherein the formulation comprises a solid thickening agent.

3. The sunscreen formulation of claim 1, wherein the metal oxide is present at a concentration of from 1 to 6 percent by weight based on the total weight of the formulation.

4. The sunscreen formulation of claim 1, wherein the semifluorinated alkane is of the formula F(CF2)n(CH2)mH, wherein n is an integer selected from 4 to 6 and m is an integer selected from 5 to 10.

5. The sunscreen formulation of claim 1, wherein the semifluorinated alkane is selected from 1-perfluorohexyl-octane (F6H8), 1-perfluorobutyl-pentane (F4H5), 1-perfluorohexyl-decane (F6H10), 1-perfluorobutyl-octane (F4H8), 1-perfluorobutyl-decane (F4H10), and combinations thereof.

6. The sunscreen formulation of claim 1, wherein the formulation comprises 50-95 wt % of the semifluorinated alkane, based on the total weight of the formulation.

7. The sunscreen formulation of claim 1, wherein the metal oxide particles have a mean particle diameter of between 1 nm and 100 nm.

8. The sunscreen formulation of claim 2, wherein the formulation comprises 1 to 40 wt % of the solid thickening agent, based on the total weight of the formulation.

9. The sunscreen formulation of claim 2, wherein the solid thickening agent is a natural or synthetic thickening agent selected from plant waxes, animal waxes, petroleum derived waxes, triglycerides, cetyl alcohol, tetradecanol, and combinations thereof.

10. The sunscreen formulation of claim 9, wherein the wax is selected from the group consisting of bees wax, lanolin wool wax, carnauba wax, candelilla wax, castor wax, rice bran wax (rice wax), spermaceti wax, jojoba oil, bran wax, montan wax, kapok wax, bay berry wax, shellac wax, sugar cane wax, paraffin wax, and ceresin wax.

11. The sunscreen formulation of claim 1, in form of an ointment.

12. The sunscreen formulation of claim 1, wherein the formulation is water-free and/or preservative-free.

13. The sunscreen formulation of claim 1, further comprising an active ingredient selected from panthenol, thymol, tea tree oil, retinol palmitate, and tocopherol.

14. A method for the prevention of skin cell damage caused by UV-radiation, comprising topically administering to the skin of a subject a composition according to claim 1.

15. A method for the prevention of skin cancer, comprising topically administering to the skin of a subject a composition according to claim 1.

16. A method for protecting the skin from sunburn, comprising topically administering to the skin of a subject a sunscreen formulation according to claim 1.

17. A kit comprising a container for holding the sunscreen formulation according to claim 1.

18. The sunscreen formulation of claim 1, wherein the metal oxide is present at a concentration of 1 to 20 percent by weight based on the total weight of the formulation, or at a concentration of 1 to 10 percent by weight based on the total weight of the formulation.

19. The sunscreen formulation of claim 1, wherein the formulation comprises a cosolvent selected from isopropanol, ethanol, liquid medium chain triglycerides, N-methyl-2-pyrrolidone, diethylene glycol monomethyl ether, diethylene glycol monoethyl ether, ethyl acetate, ethyl oleate, octyldodecanol, and diethyl sebacate.

20. The sunscreen formulation of claim 1, wherein the formulation comprises an oil component which is an oily material selected from squalane, squalene, liquid triglycerides, silicone oils, and emollient vegetable oils.

21. The sunscreen formulation of claim 20, wherein the formulation comprises the oily material squalene at a concentration of 1 to 45 percent by weight based on the total weight of the formulation.

22. The sunscreen formulation of claim 1, wherein the formulation comprises an active ingredient selected from D-panthenol, retinol palmitate, and tocopherol, and esters of each of the foregoing.

23. The sunscreen formulation of claim 20, wherein the silicone oils are selected from cyclomethicone and dimethicone.

24. The sunscreen formulation of claim 20, wherein the emollient vegetable oils are selected from olive oil, coconut oil, jojoba oil, sesame oil, avocado oil, sunflower oil, safflower oil, borage oil, corn oil, and sea buckthorn oil.

25. The sunscreen formulation of claim 1, wherein the formulation comprises an oil component which is an essential oil.

26. The sunscreen formulation of claim 1, wherein the formulation is effective to deliver the metal oxide into the stratum corneum.

27. The method according to claim 14, wherein the method provides for effective penetration of the metal oxide into the stratum corneum.

28. The method according to claim 15, wherein the method provides for effective penetration of the metal oxide into the stratum corneum.

29. The method according to claim 16, wherein the method provides for effective penetration of the metal oxide into the stratum corneum.

* * * * *

UNITED STATES PATENT AND TRADEMARK OFFICE
CERTIFICATE OF CORRECTION

PATENT NO. : 11,510,855 B2
APPLICATION NO. : 17/280055
DATED : November 29, 2022
INVENTOR(S) : Frank Löscher et al.

Page 1 of 1

It is certified that error appears in the above-identified patent and that said Letters Patent is hereby corrected as shown below:

In the Claims

Claim 7, Column 9, Line 35-36, "particles have" should be changed to --is present as metal oxide particles having--

Claim 10, Column 9, Line 47, "lanolin wool wax" should be changed to --lanolin, wool wax--

Signed and Sealed this
Fourth Day of April, 2023

Katherine Kelly Vidal
*Director of the United States Patent and Trademark Office*